(12) United States Patent
Zhu et al.

(10) Patent No.: US 6,275,731 B1
(45) Date of Patent: *Aug. 14, 2001

(54) PSEUDO-FUSION MANAGEMENT DURING AUTOMATIC CAPTURE VERIFICATION

(75) Inventors: Qingsheng Zhu, Little Canada; Jungkuk Kim, Roseville; Arthur Olive, Stacy, all of MN (US); Jan-Pieter Heemels, Oudergm (BE)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/474,193

(22) Filed: Dec. 29, 1999

Related U.S. Application Data

(63) Continuation of application No. 09/260,943, filed on Mar. 2, 1999, now Pat. No. 6,038,474.

(51) Int. Cl.[7] .................................................. A61N 1/365
(52) U.S. Cl. ................................................................ 607/9
(58) Field of Search .................................. 607/9, 28, 27

(56) References Cited

U.S. PATENT DOCUMENTS

| | | |
|---|---|---|
| 5,097,832 | 3/1992 | Buchanan . |
| 5,103,820 | 4/1992 | Markowitz . |
| 5,231,986 | 8/1993 | Bennett ................................. 607/11 |
| 5,243,979 | 9/1993 | Stein et al. ............................ 607/20 |
| 5,271,395 | 12/1993 | Wahlstrand et al. .................... 607/9 |
| 5,312,446 | 5/1994 | Holschbach et al. .................... 607/9 |
| 5,312,453 | 5/1994 | Shelton et al. ........................ 607/19 |
| 5,312,454 | 5/1994 | Roline et al. ......................... 607/22 |
| 5,336,244 | 8/1994 | Weijand ............................... 607/21 |
| 5,342,406 | 8/1994 | Thompson ............................. 607/22 |
| 5,374,282 | 12/1994 | Nichols et al. ........................ 607/18 |
| 5,441,524 | 8/1995 | Rueter et al. ......................... 607/18 |
| 5,540,729 | 7/1996 | Weijand ............................... 607/35 |
| 5,674,258 | 10/1997 | Henschel et al. ...................... 607/19 |
| 5,755,738 | 5/1998 | Kim et al. .............................. 607/9 |

OTHER PUBLICATIONS

"Practical Cardiac Diagnosis", *Cardiac Pacing*, edited by Kenneth A. Ellenbogen, M.D., "Pacemaker Timing Cycles", David L. Hayes, M.D. and Paul A. Levine, M.D., (1992).

*Primary Examiner*—Scott M. Getzon
(74) *Attorney, Agent, or Firm*—Nikolai, Mersereau & Dietz, P.A.

(57) ABSTRACT

A method for reducing the affects of intrinsic detection latency in a cardiac rhythm management device, wherein said method is initiated immediately prior to delivering a stimulation pulse to the heart tissue. A coincidence of intrinsic and cardiac rhythm management initiated stimulus or the delivery of a stimulation pulse proximate the time of an intrinsic event due to intrinsic detection latency may results in delivery of unnecessary backup stimulus and/or imprecise determination of a pacing threshold. When stimulating the heart, the timing sequence for delivering a stimulation pulse typically depends upon the timing of a previous intrinsic or device initiated event. Further, the method of the present invention reduces the affects of intrinsic detection latency thereby facilitating improved detection of capture and determination of capture threshold for minimizing power consumption while assuring therapeutic efficacy.

25 Claims, 6 Drawing Sheets

PSEUDO-FUSION MANAGEMENT DURING AUTOMATIC CAPTURE VERIFICATION

This is a Continuation of application Ser. No. 09/260,943, filed on Mar. 2, 1999 now U.S. Pat. No. 6,038,474.

BACKGROUND OF THE INVENTION

I. Field of the Invention

The present invention relates generally to a method of delivering a stimulation pulse to a patient's heart utilizing a cardiac rhythm management device, and more particularly relates to a method of reducing the affects of intrinsic detection latency during an automatic capture and/or sensing threshold determination. The method of the present invention is initiated immediately prior to delivering a stimulation pulse to the heart tissue, wherein delivery of the stimulation is terminated or delayed if the amplitude of a portion of a sensed electrogram signal exceeds a predetermined threshold. Further, the method of the present invention minimizes the delivery of stimulation pulses proximate in time with an intrinsic event due to intrinsic detection latency (pseudo-fusion).

II. Discussion of the Related Art

Cardiac rhythm management devices have enjoyed widespread use and popularity throughout time as a means for supplanting some or all of the natural pacing functions of an abnormal heart. Among the various heart abnormalities remedied by cardiac rhythm management devices include total or partial heart block, bradycardia, tachycardia, myocardial infarctions, congestive heart failure, congenital heart disorders, and various other arrhythmias and rhythm disturbances within the heart. The fundamental components of a rhythm management device include an electronic pulse generator for generating stimulation pulses to the heart and an electrode arrangement for both delivering the stimulation pulses and sensing intrinsic and/or evoked events of the heart.

Conventional rhythm management devices may be designed to stimulate the ventricle, atrium or both the ventricles and atriums depending upon the heart abnormality. Regardless of the type of rhythm management device employed to restore the heart's natural rhythm, all operate to stimulate heart tissue cells adjacent to an electrode which is employed in the heart and electrically coupled to the rhythm management device. The delivery of the stimulation pulse is often dependent upon a preprogrammed timing sequence. Without limitation, the timing sequence may, for example, depend upon sensing or failure to sense an intrinsic event during a period that is measured from a previous sensed intrinsic event or prior stimulation. If certain predetermined requirements are not met during the timing sequence, then the rhythm management device may be preprogrammed to generate and deliver a stimulation pulse to the heart. When the stimulation evokes a response in the heart, this response is typically referred to as "capture" and is a function of the positive and negative charges found in each myocardial cell within the heart.

The success of the cardiac rhythm management device in depolarizing or "capturing" the heart hinges on whether the energy of the stimulation pulse as delivered to the myocardium exceeds a threshold value. This threshold value, referred to as the capture threshold, represents the amount of electrical energy required to alter the permeability of the myocardial cells to thereby initiate cell depolarization. If the energy of the stimulation pulse does not exceed the capture threshold, then the permeability of the myocardial cells will not be altered and thus no depolarization will result. If, on the other hand, the energy of the stimulation pulse exceeds the capture threshold, then the permeability of the myocardial cells will be altered such that depolarization will result. Changes in the capture threshold may be detected by monitoring the efficacy of stimulating pulses at various energy levels.

The ability to detect capture is extremely desirable in that delivering stimulation pulses having energy far in excess of the patient's capture threshold is wasteful of the rhythm management devices limited power supply. In order to minimize current drain on the power supply, it is desirable to automatically adjust the rhythm management device such that the amount of stimulation energy delivered to the myocardium is maintained at the lowest level that will reliably capture the heart. To accomplish this, a process known as "capture verification" must be performed wherein the rhythm management device monitors to determine whether an evoked depolarization or intrinsic event occurs in the heart following the delivery of each stimulus pulse.

At times, a stimulation pulse may be delivered coincidental to a depolarization by an intrinsic beat (hereinafter referred to as "fusion" or "a fusion beat"). From a surface ECG, the fusion beats manifest themselves by a pacing spike followed by an intrinsic QRS complex. Further, due to intrinsic detection latency, a stimulation pulse may be delivered after intrinsic activation has already begun (hereinafter referred to as pseudo-fusion). From a surface ECG, it is seen that the stimulation pulse falls inside the intrinsic QRS complex. The stimulation pulses may or may not capture the myocardium. During normal delivery of a stimulation pulse, fusion and/or pseudo-fusion beats may be of little consequence except some energy loss due to unnecessary pacing output. However, during autocapture or autothresholding, the impact of fusion or pseudo-fusion can be rather different.

During autocapture or autothreshold, fusion beats may be detected as capture for amplitude-based detection methods. Thus, even though the stimulation pulse may be below threshold, the evoked response detection remains positive. As a result, the threshold may be identified at a lower amount than the actual threshold. Pseudo-fusion may be detected either as capture or non-capture depending upon timing of the occurrence of pseudo-fusion. If a stimulation pulse is delivered at an earlier portion of the QRS complex, then the stimulation pulse is more likely to be detected as capture and the consequence is the same as a fusion beat. If pseudo-fusion is detected as non-capture, a backup pulse may be issued between the QRS complex and a T wave which is undesirable.

During automatic threshold determination, pseudo-fusion beats may cause false detection of either capture or non-capture. When pseudo-fusion is detected as capture, an error in threshold measurement may arise. In many instances, occurrence of pseudo-fusion is caused by the inherent latency of sensing an intrinsic event. This latency often results from a sensing threshold level that is normally higher than front portions of the QRS complex of the endocardial signals, which prevents a detection by the rhythm management device of the front portions of the QRS complex. Other factors that may contribute to latency in intrinsic detection include sensing channel phase delay. Thus, there is a need for a method that reduces unnecessary autothresholding, error in threshold measurement, and other undesirable affects of fusion and pseudo-fusion during capture verification and autothreshold determination. There is a further need for a method that manages the timing of delivery of backup stimulation that avoids stimulating during undesirable portions of a timing cycle.

SUMMARY OF THE INVENTION

The purpose of the present invention is to provide a method of delivering a stimulation pulse to a patient's heart utilizing a cardiac rhythm management device, wherein the method reduces the affects of intrinsic detection latency during an automatic capture and/or sensing threshold determination. Those skilled in the art will appreciate that the method of the present invention may be implemented in cardiac pacers, defibrillators and other rhythm management devices. For purposes of discussion, ease of clarity, and without any limitation intended, the method of delivering stimulation pulses to a patient's heart will be described with reference to pacing a patient's heart and the timing sequences utilized in pacing the heart. Those skilled in the art will appreciate that the method of the present invention may equally apply to other rhythm management devices including defibrillators having known conventional timing sequences.

The method of the present invention utilizes a cardiac rhythm management device of suitable known construction, wherein the rhythm management device includes sensing means for sensing cardiac electrogram signals, a programmable controller coupled to receive the sensed electrogram signals, and stimulation means controlled by the controller for applying cardiac stimulation pulses to a patient's heart in response to control signals from the controller. Without limitation, the stimulation means and sensing means may comprise circuitry electrically coupled a part of the controller. The programmable controller may be programmed to function utilizing the following sequence for initiating and delivering a stimulation pulse on a beat to beat basis or during an autocapture or autothreshold determination.

First, the sensing circuit or sensing means is set to include a first sensing threshold level. As the rhythm management device receives and analyzes the cardiac electrogram signals, the controller utilizes a stimulation timing sequence that determines when the next stimulation pulse should be delivered. Those skilled in the art will appreciate that the determination of when the stimulation pulse is delivered may depend on several variables and includes a predetermined timing sequence that depends on the last sensed intrinsic event or prior delivered stimulation pulse. Within a first preset time prior to transmitting the stimulation pulse, the controller analyzes the electrogram signals to determine if an amplitude of a portion of the electrogram signals exceeds the first sensing threshold level. Without limitation, other means of known suitable construction may be utilized to determine whether an intrinsic event has been initiated. If the amplitude exceeds the first sensing threshold level, then delivery of the stimulation pulse is delayed by a second preset time. The controller then determines whether an intrinsic event occurs during the second preset time. If no intrinsic event occurs during the second preset time, then a backup stimulation pulse having a predetermined output is delivered to the heart, wherein the output of the backup stimulation pulse is sufficient such that capture of the stimulus may be assumed.

As mentioned above, the stimulation sequence may be adapted by the controller during beat to beat delivery of a stimulation pulse or when delivering a stimulation pulse during autocapture or autothreshold determination. During the stimulation sequence, if the amplitude of a portion of the electrogram signal does not exceed the first sensing threshold level within the first preset time, then the likelihood of fusion or pseudo-fusion is remote and the stimulation pulse is delivered in accordance with the prescribed timing sequence. If an intrinsic event occurs during the second preset time, a preset R—R interval of the timing sequence is extended.

The method of the present invention enhances early intrinsic detection threshold to monitor lower level intracardiac activities. Without any limitation intended, the event threshold or first sensing threshold may be set at 0.5 millivolts. One suitable determination of the sensing threshold is described in greater detail in co-pending application serial No. 09/094,773 filed Jun. 15, 1998 and assigned to the same assignee as the present application, the entire disclosure of which is incorporated herein by reference for any purpose.

Those skilled in the art will appreciate that reference to autothreshold refers to a fully automated method of measuring the stimulation threshold in either the atrium or ventricle. Autothreshold determination is distinguishable from a semi-automatic threshold test during which the operator identifies whether or not a pacing stimulus is followed by a causal depolarization. Also, as will be described in greater detail below, autothreshold determination is distinguishable from automatic capture detection or automatic output optimization. Unlike these features, autothreshold determination does not change the output values of the stimulation pulse. The controller preferably autonomously performs amplitude threshold testing periodically in order to collect a chronological trend that can be interrogated and analyzed during follow-up procedures. The threshold results can be displayed in histogram format and the programmer can suggest a safety margin based on the distribution characteristics of the threshold test results.

OBJECTS

It is accordingly a principal object of the present invention to provide a cardiac rhythm management device that reduces potential error in autocapture and autothreshold determination.

Another object of the present invention is to provide a cardiac rhythm management device that manages the timing of the delivery of stimulation pulses to initiate the delivery during predetermined portions of the timing cycle.

Yet another object of the present invention is to provide a cardiac rhythm management device that minimizes the delivery of stimulation pulses proximate in time with an intrinsic event due to intrinsic detection latency (pseudo-fusion).

Still another object of the present invention is to provide a cardiac rhythm management device that reduces the affects of fusion and pseudo-fusion during autocapture and autothreshold determination.

Without limitation, these and other objects as well as these and other advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION OF THE PREFERRED EMBODIMENT

In conjunction with the several views of the figures, details of a representative embodiment of a cardiac rhythm management device incorporating the features of the present invention will next be presented. Although the present invention may find application in a variety of implantable or external cardiac rhythm management devices, including but not limited to bradycardia pacemakers, antitachycardia pacemakers, and defibrillators, for purposes of explanation, the present invention will be described in connection with an implantable rate adaptive cardiac pacemaker. The rhythm management device may include a programmable controller having pacing and sensing circuitry and may also include read-only memory (ROM) and random access memory (RAM) communicatively coupled to the programmable controller. The cardiac rhythm management device may likewise include a transceiver cooperatively operable with an input/output module to thereby transmit and receive information to and from an external programmer. Electrodes of known suitable construction are electrically coupled to the cardiac rhythm management device and the controller contained therein, such that a stimulation pulse may be delivered to a desired location of the heart through the electrodes.

Figure 1:
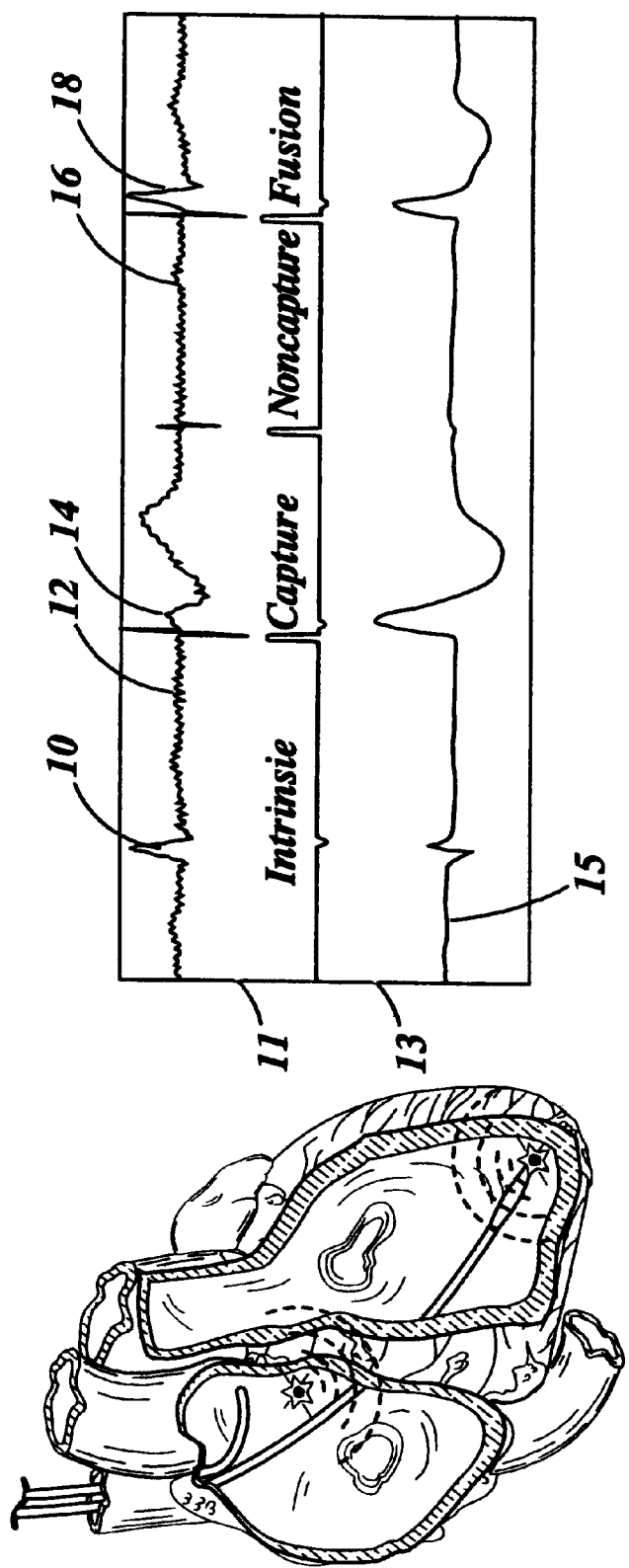
FIG. 1 is a partial sectional fragmentary view of a patient's heart having atrial and ventricular leads positioned therein, and a strip chart tracing of an electrogram waveform identifying capture, non-capture and fusion together with the corresponding strip chart tracing of a surface ECG shown for comparison and reference.
Figure 2:
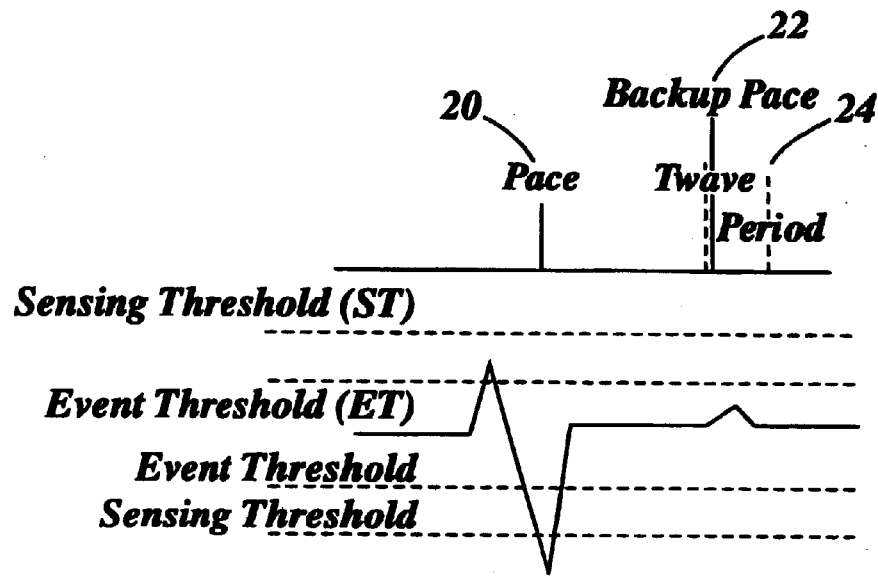
FIG. 2 is a graph showing pseudo-fusion which is detected as non-capture and resulting in pacing during an intrinsic and a backup pace proximate in time with a t-wave or vulnerable period following an intrinsic event.

Turning now to the Figures, a strip chart and graph are shown in FIGS. 1 and 2, wherein the affects of fusion and pseudo-fusion in a pacing scheme are shown. The three waveforms 11, 13, and 15 correspond to a signal transmitted from a surface electrocardiogram, an associated pacing marker, and a processed signal transmitted from an intracardiogram respectively. The timing sequence in FIG. 1 shows an intrinsic event 10 and then a period of time transpiring without a detection of another intrinsic event. After a predetermined amount of time transpires without detecting an intrinsic event, a pacing stimulus 12 is delivered which evokes a response at 14. The timing sequence shown in FIG. 1 continues to deliver pacing stimulus if an intrinsic event is not sensed within a predetermined time. The pacing stimulus 16 is delivered in accordance with the predetermined timing sequence, but results in a fusion beat because the pacing stimulus 16 is delivered at the beginning of an intrinsic event 18. Although fusion and capture may be distinguished from a surface electrocardiogram waveform, fusion and capture beats are not distinguishable from the intracardiogram waveform 15.

Figure 3:
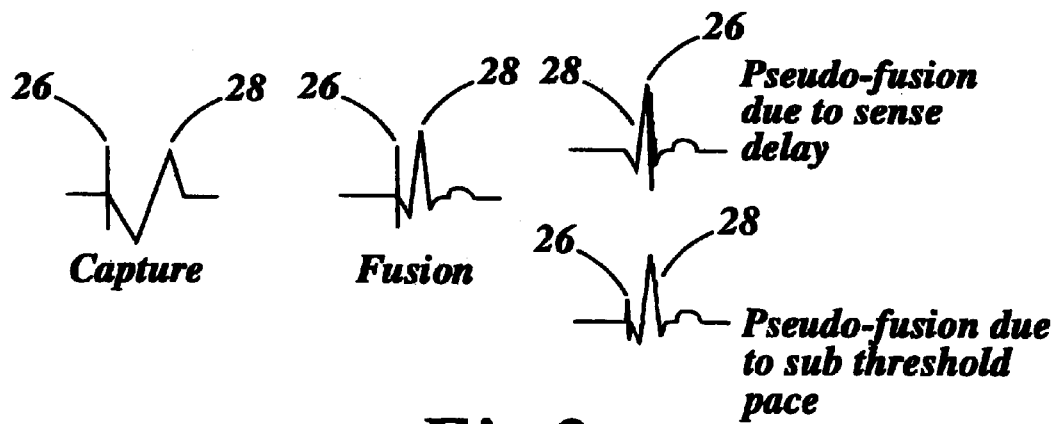
FIG. 3 are graphs showing the timing of a stimulation pulse delivered during various stages of a captured or intrinsic event.

As seen in FIG. 2, a pacing stimulus 20 may be delivered during a QRS complex, thus requiring a backup pace 22 proximate the T-wave or vulnerable period 24. Delivery of a backup pace 22 proximate the vulnerable period may lead to an undesirable arrhythmia and may be avoided by reducing fusion and pseudo-fusion during autocapture and autothreshold determination. FIG. 3 further illustrates four possible timing sequences when delivery of a pacing stimulus 26. The timing sequence identified as "Capture" shows delivery of a pacing stimulus that evokes a response. The other three timing sequences show delivery of a pacing stimulus proximate with an intrinsic event 28.

Figure 4:
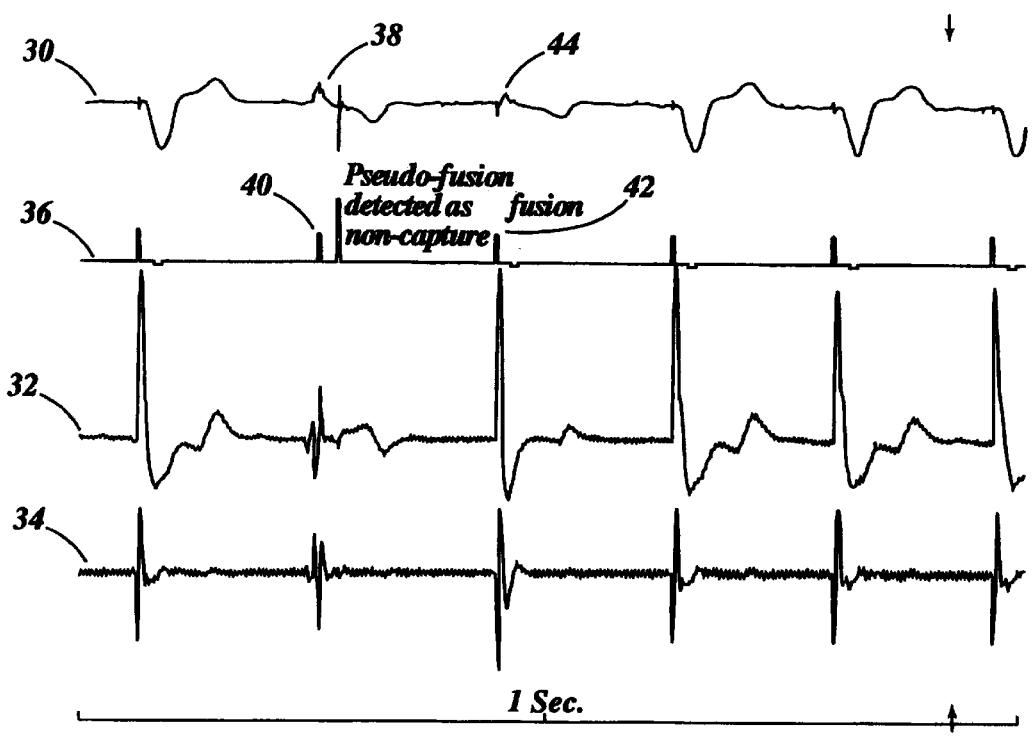
FIG. 4 shows a strip chart tracing showing "pseudo-fusions" detected as capture and non-capture and the resulting stimulation sequences, together with a strip chart tracing of a surface ECG for reference.
Figure 5:
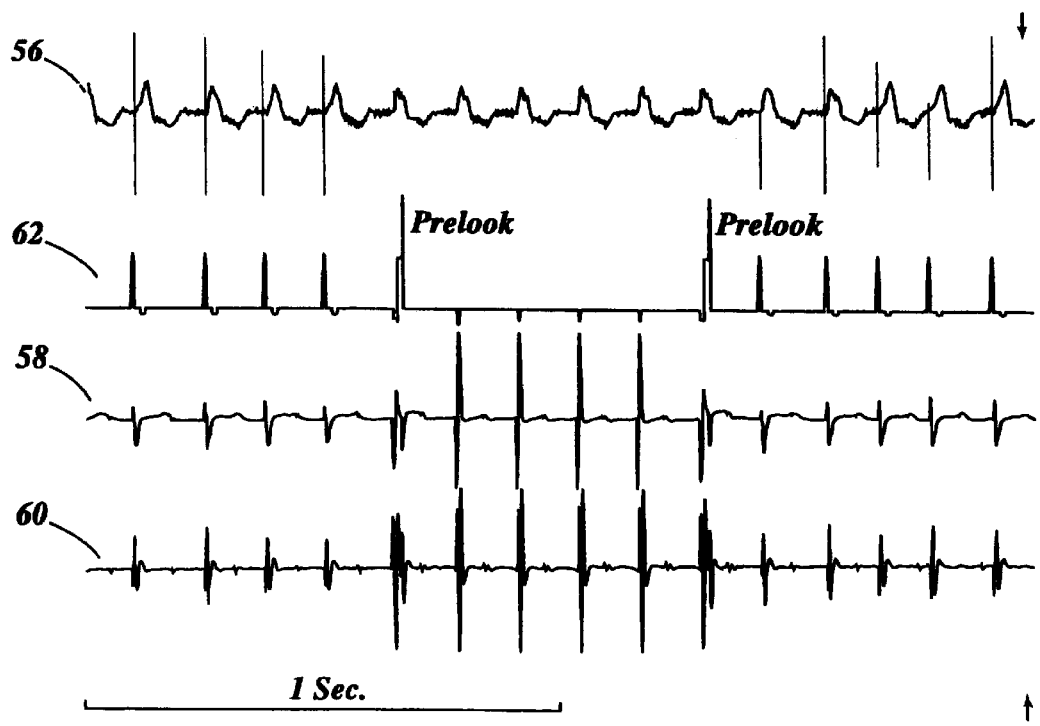
FIG. 5 shows a strip chart tracing showing the stimulation sequence including two "pre-looks", together with a strip chart tracing of a surface ECG for reference.

Referring now to FIGS. 4 and 5, strip charts of a portion of an electrogram single are shown which illustrate the affects of fusion and pseudo-fusion on a pacing interval and mode (see FIG. 4) and the implementation of the present invention to avoid fusion and pseudo-fusion (see FIG. 5). The waveforms 30–34 and associated pacing marker 36 shown in FIG. 4 illustrate the affects of a fusion or pseudo-fusion beat on the ability to accurately determine capture or autothreshold. The waveform 30 results from a signal transmitted from a surface electrocardiogram. The waveform 32 results from a signal transmitted from an intracardiogram and processed through a wideband channel of approximately 6–200 Hz. The waveform 34 results from a signal transmitted from an intracardiogram and processed through a narrower band channel of approximately 10–100 HZ. The intrinsic event identified at 38 is not identified by the pacer and therefore a pace 40 is initiated followed by a backup pace. The pacing stimulus does not evoke a response and the controller process then concludes that the pacing stimulus at 40 did not evoke a response (non-capture). The pacing stimulus at 42 immediately precedes an intrinsic event 44, which results in a fusion beat and also affects an accurate determination of capture. The waveforms 56–60 and associated pacing marker 62 shown in FIG. 5 illustrates delivery of a pacing stimulus with a pre-look. The waveform 56 results from a signal transmitted from a surface electrocardiogram. The waveform 58 results from a signal transmitted from an intracardiogram and processed through a wideband channel of approximately 6–200 Hz. The waveform 60 results from a signal transmitted from an intracardiogram and processed through a narrower band channel of approximately 10–100 HZ.

Figure 6:
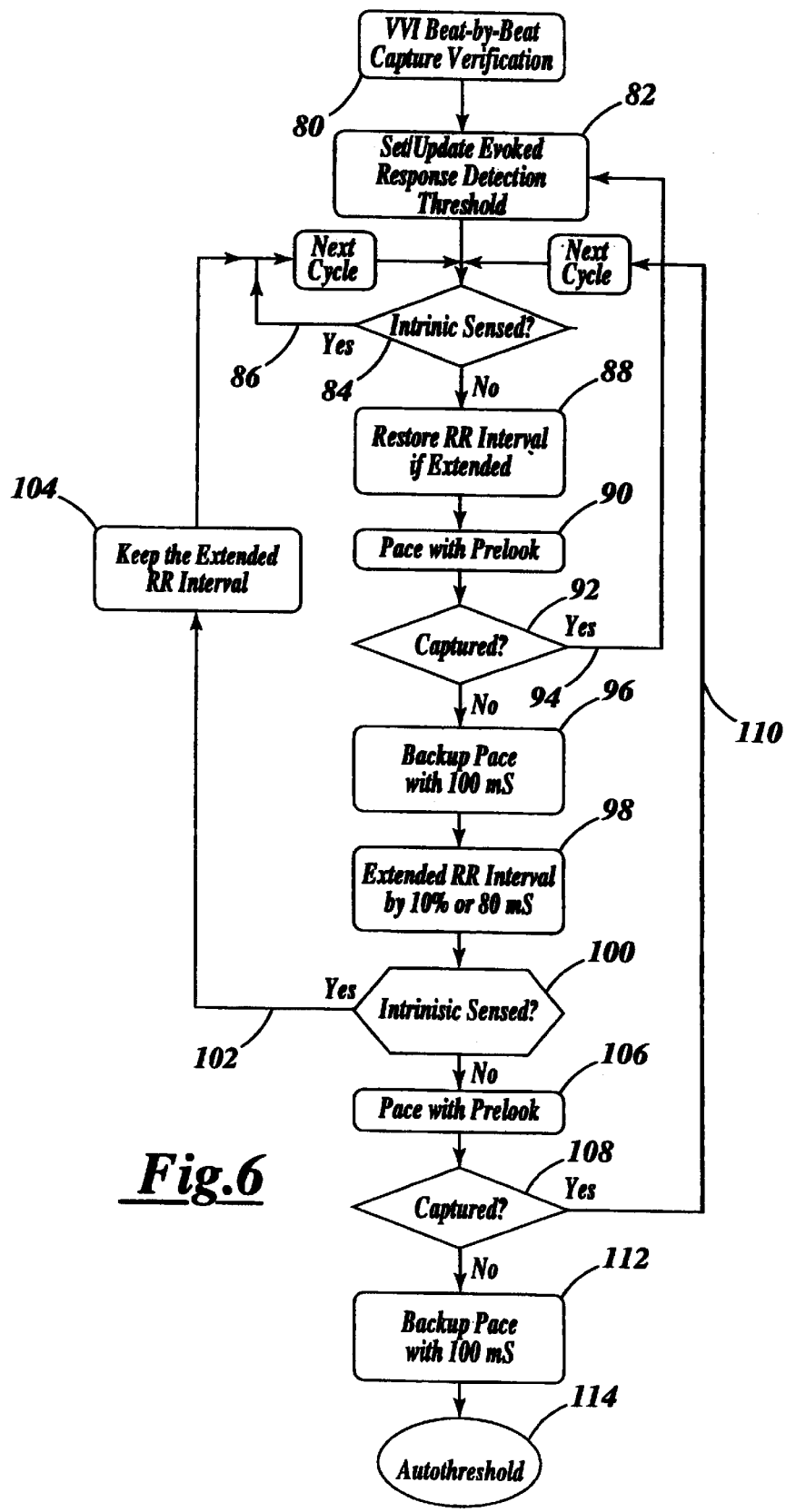
FIG. 6 is a flow chart showing a beat by beat capture verification sequence that includes delivery of a stimulation pulse with a pre-look.

Referring now to FIG. 6, without any limitation intended the sequence of VVI beat by beat capture verification utilizing the method of the present invention is shown in a flowchart diagram. A controller of the rhythm management device initiates a beat by beat capture verification at block 80. The controller then updates the evoked response detection threshold (see block 82) and a determination is made whether an intrinsic event is sensed or whether the amplitude of a selected portion of the electrogram signal exceeds the intrinsic detection threshold (see decision block 84). If an intrinsic event is sensed, the controller determines if an intrinsic event is sensed in the next cycle (see loop 86). If an intrinsic event is not sensed, then the RR interval of the various pacing intervals is restored to the preset amount (assuming that the RR interval had been extended; see block 88) and a pacing stimulation is delivered with prelook (see block 90). Delivery of a stimulation pulse with prelook will be further discussed below in conjunction with a discussion of FIG. 8. After a stimulation pulse is delivered, the controller determines whether the output or pacing stimulus results in an evoked response or capture (see decision block 92). If the stimulation pulse results in capture, the evoked response detection threshold is updated and the previous steps are repeated (see loop 94) and beat by beat pacing continues. If the pacing stimulus does not result in capture at decision block 92, then the controller initiates a backup pace within a predetermined time (see block 96) and the RR interval is extended by a predetermined amount (see block 98). Without limitation, the backup pace is preferably initiated within 100 ms and the RR interval is extended by 10% or by 80 ms. The controller then determines whether an intrinsic event occurs within a predetermined time (see decision block 100). If an intrinsic event is sensed at decision block 100, then the extended RR interval is kept and the controller determines if an intrinsic event is sensed in the next cycle (see loop 102 and block 104). If an intrinsic event is not sensed at decision block 100, then a stimulation pulse with prelook is delivered (see block 106) and capture of this pulse is determined (see decision block 108). If the stimulation with prelook results in capture then beat by beat pacing continues (see loop 110). If, however, the stimulation with prelook does not evoke a response, then a backup pace is initiated within a predetermined time (see block 112) and the controller switches to an autothreshold determination.

Figure 7:
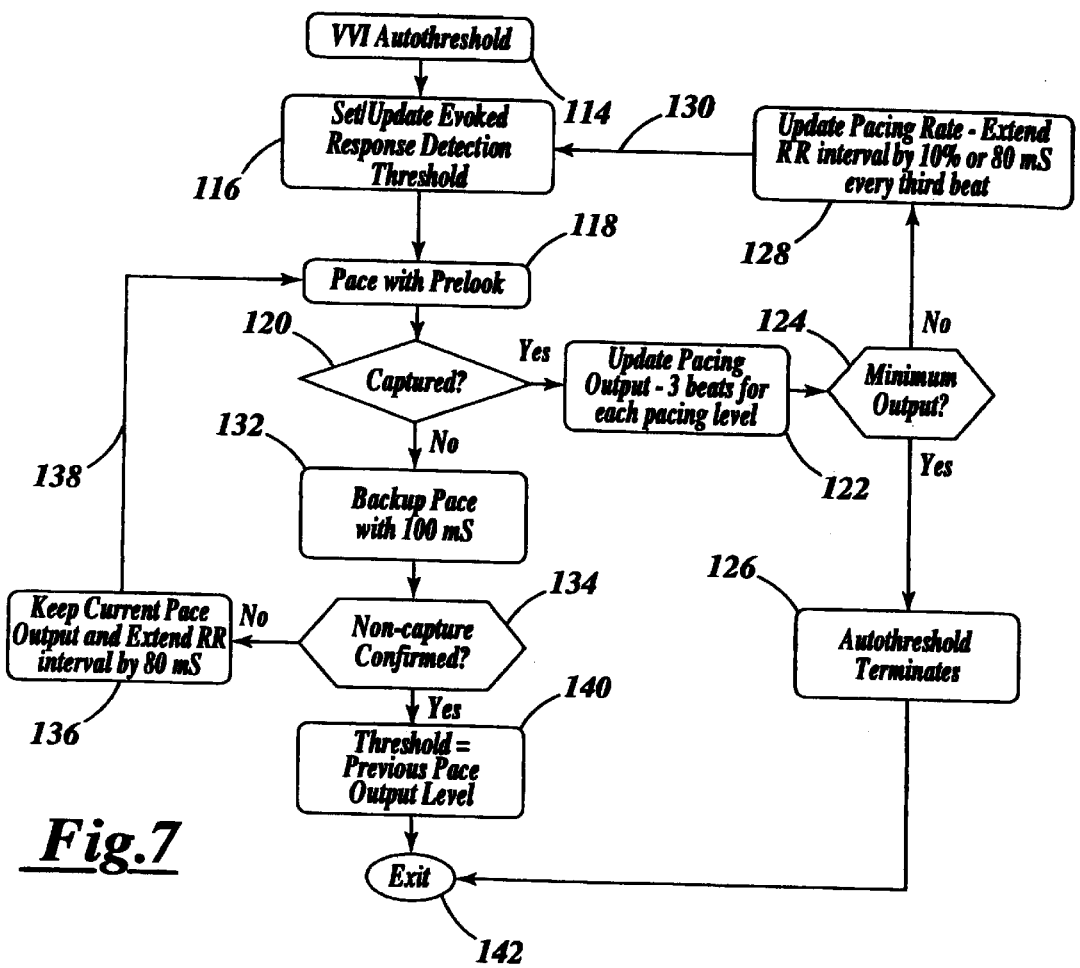
FIG. 7 is a flow chart showing an autothreshold sequence that includes delivering a stimulation pulse with a pre-look.

FIG. 7 is a flowchart representation of an autothreshold determination of the present invention. First the evoked response detection threshold is set or updated (see block 116). A stimulation pulse with prelook is delivered having a predetermined output (see block 118) and the controller determines whether the stimulation pulse evokes an intrinsic response (see decision block 120). If the stimulation pulse results in capture, the pacing output is updated (see block 122) and the pacing output is compared with a preset minimum threshold output (see decision block 124). If the pacing output is equal to the preset minimum threshold output, then autothreshold determination is terminated (see block 126). If the updated pacing output is above the minimum preset amount, then, without limitation, the pacing rate is updated for every third beat (see block 128) by extending the RR interval as described previously and autothreshold determination continues (see loop 130). If the stimulation pulse is not captured at decision block 120, then a backup pace having a predetermined output is delivered (see block 132) and the controller attempts to confirm non-capture (see decision block 134). If the controller does not confirm non-capture, then the pacing output remains the same, the RR interval is extended (see block 136) and autothreshold determination continues (see loop 138). If, however, the output results in non-capture, the threshold is set equal to the previous pace output level (see block 140) and autothreshold terminates (see block 142).

Figure 8:
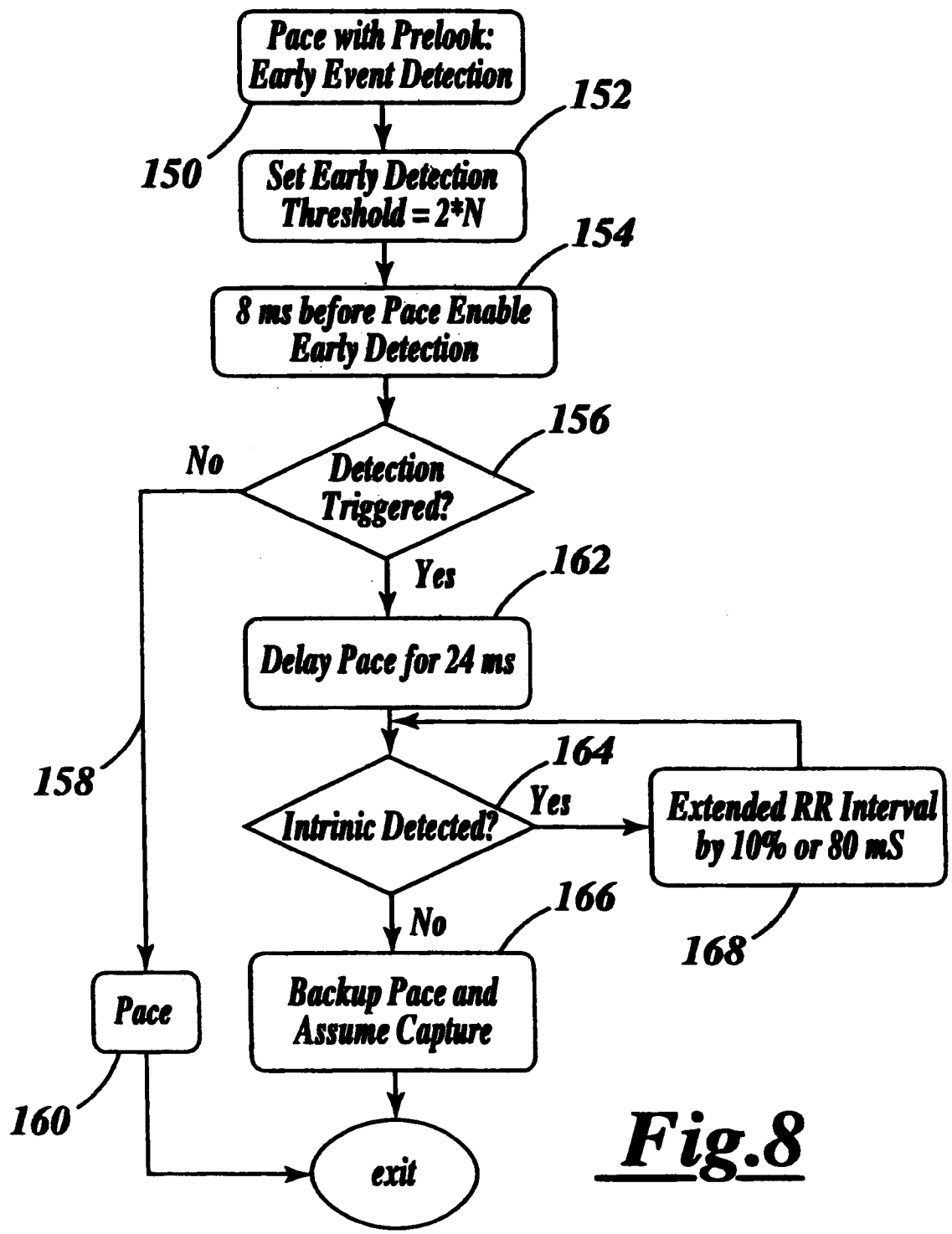
FIG. 8 is a flow chart showing the delivery of a stimulation pulse with a pre-look.

Referring now to FIG. 8, the delivery of a stimulation pulse with prelook will now be described. The controller may initiate a stimulation with prelook (see block 150) during beat to beat, autocapture or autothreshold determination. The controller first sets an early detection threshold equal to two times a predetermined amount "N" and enables the early detection threshold a predetermined time immediately before delivering the stimulation pulse (see blocks 152 and 154). Those skilled in the art will appreciate that the early detection threshold may be determined in a manner similar to determining the event threshold as described in co-pending application serial number 09/094,773 filed Jun. 15, 1998 and assigned to the same assignee as the present application, the entire disclosure of which is incorporated herein by reference for any purpose. The controller then determines whether the amplitude of a portion of the electrogram signal received during the predetermined time immediately before delivering exceeds the early detection threshold (see decision block 156). If the amplitude of a portion of the electrogram signal does not exceed the early detection threshold, then the stimulation pulse is delivered (see loop 158 and block 160). If the amplitude of a portion of the electrogram signal exceeds the early detection threshold, then delivery of the stimulation pulse is delayed by a predetermined amount (see block 162) and the portion of the electrogram signal is analyzed to determine whether an intrinsic event has occurred (see decision block). If no intrinsic event is detected then a backup pace is delivered having an output sufficient to assume capture (see block 166). If an intrinsic event is detected at decision block 164, then the RR interval is extended as described above (see block 168 and continues to be extended until an intrinsic event is not detected (see loop 170), at which time a backup pace is delivered (see block 166).

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A cardiac rhythm management device for reducing the affects of intrinsic detection latency, said device comprising means for sensing cardiac electrogram signals, a programmable controller coupled to receive the sensed electrogram signals, and stimulation means controlled by the controller for applying cardiac stimulation pulses to a patient's heart in response to control signals from the controller on a beat-to-beat basis, wherein said controller reduces the affects of intrinsic detection latency by:

(a) setting a first sensing threshold level;
   (b) identifying cardiac electrogram signals;
   (c) within a first preset time prior to transmitting a stimulation pulse, analyzing the electrogram signals to determine if an amplitude of a portion of the electrogram signals exceeds the first sensing threshold level;
   (d) if the amplitude exceeds the first sensing threshold level, then delay stimulating for a second preset time;
   (e) determining whether an intrinsic event occurs during the second preset time; and
   (f) if no intrinsic event occurs during the second preset time, delivering a backup stimulus having a predetermined output and assume capture of the backup stimulus.

2. The device in accordance with claim 1, wherein if the amplitude does not exceed the first sensing threshold level within the first preset time, then transmitting the stimulation pulse.

3. The device in accordance with claim 1, wherein said controller further reduces the affects of intrinsic detection latency by extending a preset R—R interval of the cardiac rhythm management device by a preset amount if an intrinsic event occurs during the second preset time.

4. The device in accordance with claim 3, wherein said controller reduces the affects of intrinsic detection latency during beat by beat capture verification.

5. The device in accordance with claim 3, wherein said method is utilized by the cardiac rhythm management device during an autothreshold determination.

6. The device in accordance with claim 1, wherein said first preset time is dependent upon a timing period for enabling the stimulation pulses.

7. The device in accordance with claim 6, wherein said controller reduces the affects of intrinsic detection latency during beat by beat capture verification.

8. The device in accordance with claim 6, wherein said controller reduces the affects of intrinsic detection latency during an autothreshold determination.

9. The device in accordance with claim 1, wherein said controller reduces the affects of intrinsic detection latency during beat by beat capture verification.

10. The device in accordance with claim 1, wherein said controller reduces the affects of intrinsic detection latency during an autothreshold determination.

11. A cardiac rhythm management device for reducing the affects of intrinsic detection latency, said device comprising:

(a) sensing means for sensing cardiac electrogram signals;

(b) stimulation means for applying cardiac stimulation pulses to a patient's heart; and (c) a programmable controller coupled to receive the sensed electrogram signals, said controller having a first evoked response detection threshold, wherein if no cardiac electrogram signals are detected during a predetermined period having an amplitude exceeding the detection threshold, then setting an R—R interval of the cardiac rhythm management device to a preset R—R interval and transmitting a first stimulation with a prelook, further wherein if the first stimulation with prelook results in an evoked response, then continuing stimulation at the preset R—R interval.

12. The cardiac rhythm management device according to claim 11, wherein transmitting the first stimulation with prelook includes the following steps:

aa) setting a first sensing threshold level;

bb) sensing cardiac electrogram signals;

cc) within a first preset time, analyzing the electrogram signals to determine if an amplitude of a portion of the electrogram signals exceeds the first sensing threshold level;

dd) if the amplitude exceeds the first sensing threshold level, then delay stimulating for a second preset time;

ee) determining whether an intrinsic event occurs during the second preset time; and ff) if no intrinsic event occurs during the second preset time, initiate a backup stimulus and assume capture of the stimulation pulses.

13. The cardiac rhythm management device according to claim 12, wherein when the first stimulation with prelook does not evoke response, then further including the following steps:

f) initiate a backup stimulation, extend the R—R interval of the cardiac rhythm management device by a predetermined amount and sense for an intrinsic event during a second predefined period;

g) if no intrinsic event is sensed during the second predefined period, then transmit a second stimulation with prelook; and h) determine whether the second stimulation with prelook evokes response;

i) if the second stimulation with prelook evokes response, then continue stimulation at the preset R—R interval.

14. The cardiac rhythm management device in accordance with claim 13, further including the following steps, wherein if the second stimulation with prelook does not evoke response, then initiate a backup stimulus and initiate an autothreshold.

15. The cardiac rhythm management device in accordance with claim 14, wherein said autothreshold includes stimulation with prelook.

16. A cardiac rhythm management device for reducing the affects of intrinsic detection latency, said device comprising:

(a) a sensor that senses cardiac electrogram signals;

(b) a pulse generator that transmits a cardiac stimulation pulses to a patient's heart; and (c) a programmable controller coupled to receive the sensed electrogram signals, said controller having a first sensing threshold level, wherein within a first preset time prior to transmitting a stimulation pulse, said controller analyzes the electrogram signals to determine if an amplitude of a portion of the electrogram signal exceeds the first sensing threshold level, wherein, if the amplitude exceeds the first sensing threshold level, then the controller delays stimulating for a second preset time and determines whether an intrinsic event occurs during the second preset time, wherein if no intrinsic event occurs during the second preset time, the controller delivers a backup stimulus having a predetermined output and assumes capture of the backup stimulus.

17. The cardiac rhythm management device as recited in claim 16, wherein if the amplitude does not exceed the first sensing threshold level within the first preset time, then the controller transmits the stimulation pulse.

18. The cardiac rhythm management device as recited in claim 16, wherein said controller extends a preset R—R interval by a preset amount if an intrinsic event occurs during the second preset time.

19. The cardiac rhythm management device as recited in claim 18, wherein said device reduces the affects of intrinsic detection latency during beat by beat capture verification.

20. The cardiac rhythm management device as recited in claim 18, wherein said device reduces the affects of intrinsic detection latency during an autothreshold determination.

21. The cardiac rhythm management device as recited in claim 16, wherein said first preset time is dependent upon a timing period for enabling the stimulation pulses.

22. The cardiac rhythm management device as recited in claim 21, wherein said device reduces the affects of intrinsic detection latency during beat-by-beat capture verification.

23. The cardiac rhythm management device as recited in claim 21, wherein said device reduces the affects of intrinsic detection latency during an autothreshold determination.

24. The cardiac rhythm management device as recited in claim 16, wherein said device reduces the affects of intrinsic detection latency during beat by beat capture verification.

25. The cardiac rhythm management device as recited in claim 16, wherein said device reduces the affects of intrinsic detection latency during an autothreshold determination.

* * * * *